US006428324B1

(12) United States Patent
Parrington

(10) Patent No.: US 6,428,324 B1
(45) Date of Patent: *Aug. 6, 2002

(54) RNA RESPIRATORY SYNCYTIAL VIRUS VACCINES

(75) Inventor: Mark Parrington, Bradford (CA)

(73) Assignee: Aventis Pateur Limited, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/486,553

(22) PCT Filed: Sep. 3, 1998

(86) PCT No.: PCT/CA98/00840

§ 371 (c)(1),
(2), (4) Date: May 24, 2000

(87) PCT Pub. No.: WO99/11808

PCT Pub. Date: Mar. 11, 1999

Related U.S. Application Data

(63) Continuation-in-part of application No. 08/923,558, filed on Sep. 4, 1997, now Pat. No. 6,060,308.

(51) Int. Cl.$^7$ ............................................. C12N 15/00
(52) U.S. Cl. .............................. 0435/320.1; 424/186.1; 424/199.1; 424/204.1; 424/211.1; 424/93.6; 435/69.1; 536/23.72
(58) Field of Search ................................ 424/93.2, 93.6, 424/184.1, 186.1, 199.1, 204.1, 211.1; 435/69.1, 173.3, 235.1, 320.1, 455; 536/23.72; 935/32

(56) References Cited

U.S. PATENT DOCUMENTS

| 5,284,764 | A |   | 2/1994  | Wathen         | 435/240.2 |
| 5,614,372 | A |   | 3/1997  | Hans et al.    | 435/7.23  |
| 5,814,482 | A |   | 9/1998  | Dubensky       |           |
| 5,843,723 | A |   | 12/1998 | Dubensky       |           |
| 5,843,913 | A |   | 12/1998 | Li             |           |
| 6,060,308 | A | * | 5/2000  | Parrington     | 435/320.1 |

FOREIGN PATENT DOCUMENTS

| WO | WO 95/27069 | 10/1995 |
| WO | WO 96 17072 | 6/1996  |
| WO | WO 96 40945 | 12/1996 |

OTHER PUBLICATIONS

Paul et al. Expression of HIV–1 envelope glycoproteins by Semlike Forest virus vectors. AIDS Research and Human Retroviruses (1993), pp 963–970. (abstract only).*
McIntosh K. and Chanock R.M. in Fields B.N. and Knipe D.M. (eds). Virology. Raven Press, New York, 1990, pp. 1045–1072.
Murphy B.R., Hall S.L., Kulkarni A.B., Crowe J.E., Collins P.L., Connors M., Karron R.A. and Chanock R.M., Virus Res 32, 13–36, 1994.
Osterweil D. and Norman D., Am Geriat Soc 36, 659–662, 1990.
Agius G., Dindinand G., Biggar R.J., Peyre R., Vaillant V., Ranger S., Poupet J.Y., Cisse M.F. and Casters M., J Med Virol 30, 117–127, 1990.
Katz S.L. in New vaccine development establishing priorities vol. 1. National Academic Press, Washington, 1985, pp. 3974 09.
Wertz G.W. and Sullender W.M., Biotechnology 20, 151–176, 1992.
Fulginiti V.A., Eller J.J., Sieber O.F., Joyner J.W., Minamitani M. and Meiklejohn G., Am i Epidemiol 89, 449–463, 1969.
Belshe R.B., Van Voris L.P. and Mufson M.A., J Infect Dis 145, 311–319, 1982.
Kim R.M., Arrobio J.O., Pyles G., Brandt C.D., Camargo E., Chanock R.M. and Parrott R.H., Pediatrics 48, 745–755, 1971.
Gruber C. and Levine S., J Gen Virol 64, 825–832, 1983.
Olmstead R.A., Elango N. and Prince G.A., Proc Natl Acad Sci USA 83, 7462–7466, 1991.
Parrington M., Cockle S., Wyde P., Du R.–P., Snell E., Yan W.–Y., Wang Q., Gisonni L., Sanhueza S., Ewasyshyn M. and Klein M., Virus Genes 14, 63–72, 1997.
Fulginiti, V.A., Eller, J.J., Sieber, O.F., Joyner, J.W., Minamitani, M. and Meiklejohn, G. (1969) Am. J. Epidemiol. 89 (4), 435–448.
Chin, J., Magoffin, R.L., Shearer, L.A., Schieble, J.H. and Lennette, E.H. (1969) Am. J. Epidemiol. 89 (4), 449–463.
Jensen, K.E., Peeler, B.E. and Dulworth, W.G. (1962) J. Immunol. 89, 216–226.
Murphy, B.R., Prince, G.A., Collins, P.L., Van Wyke –Coelingh, K., Olmsted, R.A., Spriggs, M.K., Parrott, R.H., Kim, H.–Y., Brandt, C.D. and Chanock, R.M. (1988) Vir. Res. 11, 1–15.
Hall, S.L., Sarris, C.M., Tierney, E.L., London, W.T., and Murphy, B.R. (1993) J. Infect. Dis. 167, 958–962.

(List continued on next page.)

Primary Examiner—Jeffrey Stucker
Assistant Examiner—Ulrike Winkler
(74) Attorney, Agent, or Firm—Sim & McBurney

(57) ABSTRACT

A vector comprising a first DNA sequence which is complementary to at least part of an alphavirus RNA genome and having the complement of complete alphavirus DNA genome replication regions, a second DNA sequence encoding a paramyxovirus protein, particularly a respiratory syncytial virus fusion (RSV F) protein or a RSV F protein fragment that generates antibodies that specifically react with RSV F protein, the first and second DNA sequences being under the transcriptional control of a promoter is described. Such vector may be used to produce an RNA transcript which may be used to immunize a host, including a human host, to protect the host against disease caused by paramyxovirus, particularly respiratory syncytial virus, by administration to the host. The RNA transcript may be formed by linearization of the vector through cleavage at a unique restriction site in a plasmid vector and then transcribing the linear molecule.

22 Claims, 8 Drawing Sheets

OTHER PUBLICATIONS

Belshe, R.B., Karron, R.A., Newman, F.K., Anderson, E.L., Nugent, S.L., Steinhoff, M., Clements, M.L., Wilson, M.H., Hall, S.L., Tierney, E.L. and Murphy, B.R. (1992) J. Clin. Microbiol. 30 (8), 2064–2070.

Hall, S.L., Stokes, A., Tierney, E.L., London, W.T., Belshe, R.B., Newman, F.C. and Murphy, B.R. (1992) Vir. Res. 22, 173–184.

Van Wyke Coelingh, K.L., Winter, C.C., Tierney, E.L., London, W.T. and Murphy, B.R. (1988) J. Infect. Dis. 157 (4), 655–662.

Ray, R., Novak, M., Duncan, J.D., Matsuoka, Y. and Compans, R.W. (1993) J. Infect. Dis. 167, 752–755.

Ray, R., Brown, V.E. and Compans, R.W. (1985) J. Infect. Dis. 152 (6), 1219–1230.

Ray, R. and Compans, R.W. (1987) J. Gen. Virol. 68, 409–418.

Ray, R., Glaze, B.J., Moldoveanu, Z. and Compans, R.W. (1988) J. Infect. Dis. 157 (4), 648–654.

Ray, R., Matsuoka, Y., Burnett, T.L., Glaze, B.J. and Compans, R.W. (1990) J. Infect. Dis. 162, 746–749.

Ray, R., Glaze, B.J. and Compans, R.W. (1988) J. Virol. 62 (3), 783–787.

Ewasyshyn, M., Caplan, B., Bonneau A.–M., Scollard, N., Graham, S., Usman, S. and Klein, M. (1992) Vaccine 10 (6), 412–420.

Ambrose, M.W., Wyde, P.R., Ewasyshyn, M., Bonneau, A.–M., Caplan, B., Meyer, H.L. and Klein, M. (1991) Vaccine 9, 505–511.

Kasel, J. A., Frank, A.L., Keitel, W.H., Taber, L.H., Glezen W.P. J. Virol. 1984; 52:828–32.

Lehman, D.J., Roof, L.L., Brideau, R.J., Aeed, P.A., Thomsen, D.R., Elhammer, A.P., Wathen, M.W. and Homa, F.L. (1993) J. Gen. Virol. 74, 459–469.

Brideau, R.J., Oien, N.L., Lehman, D.J., Homa, F.L. and Wathen, M.W. (1993) J. Gen. Virol. 74, 471–477.

Ebata, S.N., Prevec, L., Graham, F.L. and Dimock, K. (1992) Vir. Res. 24, 21–33.

Hall, S.L., Murphy, B.R. and Van Wyke Coelingh, K.L. (1991) Vaccine 9, 659–667.

Strauss E.G and Strauss J.H., in Schlesinger S.S. and Schlesinger M.i. (eds). The Togaviridae and Flaviviridae. Plenum Press, New York, 1986, pp. 35–90.

Dalemans W., Delers A., Delmelle C., Denamur F., Meykens R., Thiriart C., Veenstra S., Francotte M., Bruck C. and Cohen J., Annals New York Academy of Sciences, 255–256, 1996.

Tang et al, Nature 1992, 356: 152–154.

Furth et al, Analytical Biochemistry, 1992, 205: 365–368.

Du, R.P. et al., Biotechnology 12, 813–818, 1994.

Graham B.S., Perkins M.D., Wright P.F. and Karzon D.T., J. Mod. Virol. 26, 153–162, 1988.

Davis et al. Vaccine 12, 1503–1509, 1994.

Prince, G.A., et al. Am. J. Pathol. 93, 771–790, 1978.

Liljestroem, P. et al, Biotechnology, vol. 9, Dec. 1991, pp. 1356–1361.

Schlesinger, S., Trends in Biotechnology, vol. 11, No. 1, Jan. 1, 1993 pp. 18–22.

Zhou, X. et al, Vaccine, vol. 12, No. 16, 1994, pp. 1510–1514.

Bousse, et al., 1997 Virology 232 pp. 44–52.

* cited by examiner

```
  0 GATCCGCGGCGGCGGAATTCGGCACGAGTAACAATGGAGTTGCTAATCCTCAAAGCAAATG   60
  0                                                                 9
 61 CAATTACCACAATCCTCACTGCAGTCACATTTGTTTTGCTTCTGGTCAAAACATCACTG    120
 10                                                                29
121 AAGAATTTTATCAATCAACATGCAGTTAGCAAAGGCTATCTTAGTGCTCTGAGAA        180
 30                                                                49
181 CTGGTTGGTATACCAGTGTTATAACTATAGAATTAAGTAATATCAAGGAAAATAAGTGTA   240
 50                                                                69
241 ATGGAACAGATGCTAAGGTAAAATTGATAAACAAGAATTAGATAAATATAAAAATGCTG    300
 70                                                                89
301 TAACAGAATTGCAGTTGCTCATGCAAAGCACCACCAACAATCGAGCCAGAAGAG         360
 90                                                               109
481 AACTACCAAGGTTTATGAATTATACACTCAACAATGCCAAAAAAACCAATGTAACATTAA   420
110                                                               129
421 GCAAGAAAAGGAAAAGAAGATTTCTTGGTTTTTTTGTTAGGTGTTGGATCTGCAATCGCCA  480
130                                                               149
481 GTGGGCGTTGCTGTATCTAAGGTCCTGCACCTAGAAGGGGAAGTGAACAAGATCAAAAGTG  540
150                                                               169
```

FIG.2B

```
541  CTCTACTATCCACAAACAAGGCTGTAGTCAGCTTATCAAATGGAGTTAGTGTCTTAACCA    600
170                                                                 189
601  GCAAAGTGTTAGACCTCAAAAACTATATAGATAAACAATTGTTACCTATTGTGAACAAGC    660
190                                                                 209
661  AAAGCTGCAGCATATCAAATATAGAAACTGTGATAGAGTTCCAACAAAAGAACAACAGAC    720
210                                                                 229
721  TACTAGAGATTACCAGGGAATTTAGTGTGTTAATGCAGGTGTAACTACACCTGTAAGCACTT   780
230                                                                 249
781  ACATGTTAACTAATAGTGAATTATTGTCATTAATCAATGATATGCCTATAACAAATGATC   840
250                                                                 269
841  AGAAAAAGTTAATGTCCAACAATGTTCAAATAGTTAGACAGCAAAGTTACTCTATCATGT   900
270                                                                 289
901  CCATAATAAAGAGGAAGTCTTAGCATATGTAGTACAATTACCACTATATGGTGTTATAG    960
290                                                                 309
961  ATACACCCTGTTGGAAACTACACACATCCCCTCTATGTACAACAACAAAAGAAGGGT      1020
310  D  T  P  C  W  K  L  H  T  S  P  L  C  T  T  N  T  K  E  G     329
1021 CCAACATCTGTTTAACAAGAACTGACAGAGGATGGTACTGTGACAATGCAGGATCAGTAT   1080
330  S  N  I  C  L  T  R  T  D  R  G  W  Y  C  D  N  A  G  S  V    349
```

FIG.2C

```
1081 CTTTCTTCCCACAAGCTGAAACATGTAAAGTTCAATCAAATCGAGTATTTGTGACACAA 1140
 350   S  F  F  P  Q  A  E  T  C  K  V  Q  S  N  R  V  F  C  D  T   369
1141 TGAACAGTTTAACATTACCAAGTGAAATAAATCTCTGCAATGTTGACATATTCAACCCCA 1200
 370   M  N  S  L  T  L  P  S  E  I  N  L  C  N  V  D  I  F  N  P   389
1201 AATATGATTGTAAAATTATGACTTCAAAAACAGATGTAAGCAGCTCCGTTATCACATCTC 1260
 390   K  Y  D  C  K  I  M  T  S  K  T  D  V  S  S  S  V  I  T  S   409
1261 TAGGAGCCATTGTGTCATGCTATGGCAAAACTAAATGTACAGCATCCAATAAAAATCGTG 1320
 410   L  G  A  I  V  S  C  Y  G  K  T  K  C  T  A  S  N  K  N  R   429
1321 GAATCATAAAGACATTTTCTAACGGGTGCGATTATGTATCAAATAAAGGGATGGACACTG 1380
 430   G  I  I  K  T  F  S  N  G  C  D  Y  V  S  N  K  G  M  D  T   449
1381 TGTCTGTAGGTAACACATTATATTATGTAAATAAATTTCTATGACCCATTAGTATTCCCCTCTGATGAATTTGATG 1440
 450   V  S  V  G  N  T  L  Y  Y  V  N  K  Q  E  G  K  S  L  Y  V   469
1441 AAGGTGAACCAATATCTCAAGTCAACGAGAAGATTAACCAGAGCCTAGCATTTATTCGTAAATCCG 1500
 470   K  G  E  P  I  I  N  F  Y  D  P  L  V  F  P  S  D  E  F  D   489
1501 CATCAATATCTCAAGTCAACGAGAAGATTAACCAGAGCCTAGCATTTATTCGTAAATCCG 1560
 490   A  S  I  S  Q  V  N  E  K  I  N  Q  S  L  A  F  I  R  K  S   509
1561 ATGAATTATTACATAATGTAAATGCTGGTAAATCCACCAAATATCATGACTTGATAAT    1620
 510   D  E  L  L  H  N  V  N  A  G  K  S  T  T  N  I  M  T  *     527

1621 GAG                                                           1623
```

RNA RESPIRATORY SYNCYTIAL VIRUS VACCINES

This application is a U.S. National Phase filing pursuant to 35 U.S.C 371 of PCT/CA98/00840 filed Sep. 3, 1998 which itself is a continuation-in-part of U.S. patent application Ser. No. 08/923,558 filed Sep. 4, 1997 (now U.S. Pat. No.: 6,060,308)."

FIELD OF INVENTION

The present invention relates to the field of paramyxoviridae vaccines and is particularly concerned with vaccines comprising RNA encoding the fusion (F) protein of respiratory syncytial virus (RSV).

BACKGROUND OF THE INVENTION

Human respiratory syncytial virus (RSV) has been identified as a major pathogen responsible for severe respiratory tract infections in infants, young children and the institutionalized elderly (refs. 1,2,3,4—throughout this application, various references are cited in parentheses to describe more fully the state of the art to which this invention pertains. Full bibliographic information for each citation is found at the end of the specification, immediately preceding the claims. The disclosures of these references are hereby incorporated by reference into the present disclosure). Global mortality and morbidity figures indicate that there is an urgent need for an efficacious RSV vaccine (refs. 5,6). In the USA alone, approximately 100,000 children are hospitalized annually with severe cases of pneumonia and bronchiolitis resulting from an RSV infection. Inpatient and ambulatory care for children with RSV infections has been estimated to cost in excess of $340 million each year in the USA. The World Health Organization (WHO) and the National Institute of Allergy and Infectious Disease (NIAID) vaccine advisory committees have ranked RSV second only to HIV for vaccine development. Both the annual morbidity and mortality figures as well as the staggering health care costs for managing RSV infections have provided the incentive for aggressively pursuing the development of efficacious RSV vaccines. However, such a vaccine is still not available.

Formalin-inactivated (FI-RSV) and live attenuated RSV vaccines have failed to demonstrate efficacy in clinical trials (refs. 7,8,9,10). Moreover, the formalin-inactivated RSV vaccine caused enhanced disease in some children following exposure to wild-type RSV (refs. 7,8,9,10). Elucidation of the mechanism(s) involved in the potentiation of RSV disease is important for the design of safe RSV vaccines, especially for the seronegative population. Recent experimental evidence suggests that an imbalance in cell-mediated responses may contribute to immunopotentiation. Enhanced histopathology observed in mice that were immunized with the FI-RSV and challenged with virus could be abrogated by depletion of CD4+ cells or both interleukin-4 (IL-4) and IL-10.

The RSV fusion (F) glycoprotein is one of the major immunogenic proteins of the virus. This envelope glycoprotein mediates both fusion of the virus to the host cell membrane and cell-to-cell spread of the virus (ref. 1). The F protein is synthesized as a precursor ($F_0$) molecule which is proteolytically cleaved to form a disulphide-linked dimer composed of the N-terminal $F_2$ and C-terminal $F_1$ moieties (ref. 11). The amino acid sequence of the F protein is highly conserved among RSV subgroups A and B and is a cross-protective antigen (refs. 6,12). In the baculovirus expression system, a truncated secreted version of the RSV F protein has been expressed in Trichoplusia ni insect cells (ref. 13). The recombinant protein was demonstrated to be protective in the cotton rats (ref. 13).

Studies on the development of live viral vaccines and glycoprotein subunit vaccines against parainfluenza virus infection are being pursued. Clinical trial results with a formalin-inactivated PIV types 1,2,3 vaccine demonstrated that this vaccine was not efficacious (refs. 14, 15, 16). Further development of chemically-inactivated vaccines was discontinued after clinical trials with a formalin-inactivated RSV vaccine demonstrated that not only was the vaccine not effective in preventing RSV infection but many of the vaccinees who later became infected with RSV suffered a more serious disease. Most of parainfluenza vaccine research has focussed on candidate PIV-3 vaccines (ref. 17) with significantly less work being reported for PIV-1 and PIV-2. Recent approaches to PIV-3 vaccines have included the use of the closely related bovine parainfluenza virus type 3 and the generation of attenuated viruses by cold-adaptation of the virus (refs. 18, 19, 20, 21).

Another approach to parainfluenza virus type 3 vaccine development is a subunit approach focusing on the surface glycoproteins hemagglutinin-neuraminidase (HN) and the fusion (F) protein (refs. 22, 23, 24). The HN antigen, a typical type II glycoprotein, exhibits both haemagglutination and neuraminidase activities and is responsible for the attachment of the virus to sialic acid containing host cell receptors. The type I F glycoprotein mediates fusion of the viral envelope with the cell membrane as well as cell to cell spread of the virus. It has recently been demonstrated that both the HN and F glycoproteins are required for membrane fusion. The F glycoprotein is synthesized as an inactive precursor (F) which is proteolytically cleaved into disulfide-linked F2 and F1 moieties. While the HN and F proteins of PIV-1, -2 and -3 are structurally similar, they are antigenically distinct. Neutralizing antibodies against the HN and F proteins of one of PIV type are not cross-protective. Thus, an effective PIV subunit vaccine must contain the HN and F glycoproteins from the three different types of parainfluenza viruses. Antibody to either glycoprotein is neutralizing in vitro. A direct correlation has been observed between the level of neutralizing antibody titres and resistance to PIV-3 infections in infants. Native subunit vaccines for parainfluenza virus type 3 have investigated the protectiveness of the two surface glycoproteins. Typically, the glycoproteins are extracted from virus using non-ionic detergents and further purified using lectin affinity or immunoaffinity chromatographic methods. However, neither of these techniques may be entirely suitable for large scale production of vaccines under all circumstances. In small animal protection models (hamsters and cotton rats), immunization with the glycoproteins was demonstrated to prevent infection with live PIV-3 (refs. 25, 26, 27, 28, 29). The HN and F glycoproteins of PIV-3 have also been produced using recombinant DNA technology. HN and F glycoproteins have been produced in insect cells using the baculovirus expression system and by use of vaccinia virus and adenovirus recombinants (refs. 30, 31, 32, 33, 34). In the baculovirus expression system, both full-length and truncated forms of the PIV-3 glycoproteins as well as a chimeric F-HN fusion protein have been expressed. The in recombinant proteins have been demonstrated to be protective in small animal models (see WO91/00104, U.S. application Ser. No. 07/773,949 filed Nov. 29, 1991, assigned to the assignee hereof).

Semliki Forest virus (SFV) is a member of the Alphavirus genus in the Togaviridae family. The mature virus particle contains a single copy of a ssRNA genome with a positive polarity that is 5'-capped and 3'-polyadenylated. It functions as an mRNA and naked RNA can start an infection when introduced into cells. Upon infection/transfection, the 5' two-thirds of the genome is translated into a polyprotein that is processed into the four nonstructural proteins (nsP1 to 4) by self cleavage. Once the ns proteins have been synthesized they are responsible for replicating the plus-strand (42S) genome into full-length minus strands (ref. 35). These minus-strands then serve as templates for the synthesis of new plus-strand (42S) genomes and the 26S subgenomic mRNA (ref. 35). This subgenomic mRNA, which is colinear with the last one-third of the genome, encodes the SFV structural proteins. In 1991 Liljestrom and Garoff (ref. 36) designed a series of expression vectors based on the SFV cDNA replicon. These alphavirus vectors also are described in WO 92/10578, the disclosure of which is incorporated herein by reference. These vectors had the virus structural protein genes deleted to make the way for heterologous inserts, but preserved the nonstructural coding region for production of the nsP1 to 4 replicase complex. Short 5' and 3' sequence elements required for RNA replication were also preserved. A polylinker site was inserted downstream from the 26S promoter followed by translation stop sites in all three frames. An SpeI site was inserted just after the 3' end of the SFV cDNA for linearization of the plasmid for use in vitro transcription reactions.

Injections of SFV RNA encoding a heterologous protein have been shown to result in the expression of the foreign protein and the induction of antibody in a number of studies (refs. 37, 38). The use of SFV RNA inoculation to express foreign proteins for the purpose of immunization would have several of the advantages associated with plasmid DNA immunization. For example, SFV RNA encoding a viral antigen may be introduced in the presence of antibody to that virus without a loss in potency due to neutralization by antibodies to the virus. Also, because the protein is expressed in vivo the protein should have the same conformation as the protein expressed by the virus itself. Therefore, concerns about conformational changes which could occur during protein purification leading to a loss in immunogenecity, protective epitopes and possibly immunopotentiation, could be avoided by nucleic acid immunization.

Immunization with SFV RNA also has several unique advantages over plasmid DNA immunization. SFV is one of the most efficiently replicating viruses known. After a few hours, up to 200,000 copies of the plus-RNAs can be made in a single cell. These SFV RNAs are so abundant almost all of the cells ribosomes are enrolled in the synthesis of the SFV encoded proteins, thus overtaking host cell protein synthesis (ref. 36). Therefore, it should require a smaller dose of SFV RNA and less time to achieve a protective effect as compared to plasmid DNA immunization. Secondly, RNA, unlike DNA, poses no potential threat of integrating into the cell genome. Thirdly, SFV RNA replication and expression occurs only in the cytoplasm of the cell. Therefore, problems involving nuclear transport and splicing associated with nucleus-based expression systems (DNA immunization) are absent. Fourthly, since the replication of the SFV RNA is transient and RNA is quite labile, the SFV RNA will not persist for long periods after immunization like DNA plasmids.

In WO 95/27044, the disclosure of which is incorporated herein by reference, there is described the use of alphavirus cDNA vectors based on cDNA complementary to the alphavirus RNA sequence. Once transcribed from the cDNA under transcriptional control of a heterlogous promoter, the alphavirus RNA is able to self-replicate by means of its own replicase and thereby amplify the copy number of the transcribed recombinant RNA molecules.

In copending U.S. patent application Ser. No. 08/476,397 filed Jun. 7, 1995, now U. S. Pat. No. 6,019,980 (WO 96/40945), assigned to the assignee hereof and the disclosure of which is incorporated herein by reference, there are described certain plasmid constructs used for DNA immunization which include forms of the RSV F gene. As seen therein, one plasmid pXL2 conferred complete protection on mice to challenge by live RSV when administered intranasally. This plasmid contains a gene encoding a truncated RSV F protein lacking the transmembrane portion of the protein, the immediate-early promoter enhancer and intron sequences of human cytomegatrovius (CMV) and the intron II sequences of rabbit β-globin to prevent aberrant splicing. The same plasmid construct but without the intron II sequences of rabbit β-globin, i.e. pXL1, provided only partial protection. Similarly, plasmid construct pXL4, which is the same as pXL2 except the RSV F gene encodes the full length RSV protein, provided partial protection while the corresponding construct lacking the intron II sequence of rabbit β-globin, i.e. pXL3, conferred no protection.

These data show that the absence of elements to reduce aberrant splicing adversely affects the, protective ability of the plasmid. Aberrant splicing occurs during nuclear transcription of DNA to RNA. By employing RNA transcripts for immunization, the need for nuclear processing is avoided and aberrant splicing is unable to occur. This enables the use of the intron II sequences from non-human sources to be avoided.

The use of RNA transcripts for administration to the host enables there to be obtained total protection to challenge using a lower dose in less time than when employing the DNA plasmids described in U.S. Ser. No. 08/476,397 (WO 96/40945). The use of the RNA transcripts avoids persistence of DNA in the immunized host and potential integration.

The ability to immunize against disease caused by RSV by immunization with naked SFV RNA encoding the RSV F protein, particularly the secreted version of the RSV F protein, was unknown before the present invention and could not be predicted on the basis of the known prior art. Infection with RSV leads to serious disease. It would be useful and desirable to provide improved vectors for in vivo administration of immunogenic preparations, including vaccines, for protection against disease caused by RSV. In particular, it would be desirable to provide vaccines that are immunogenic and protective in the elderly and paediatric human populations, including seronegative infants, that do not cause disease enhancement (immunopotentiation).

SUMMARY OF THE INVENTION

The present invention provides novel immunogenic materials and immunization procedures based on such novel materials for immunizing against disease caused by paramyxoviridae, including respiratory syncytial virus and parainfluenza virus. In particular, the present invention is directed towards the provision of RNA vaccines against disease caused by infection with paramyxoviridae.

In accordance with one aspect of the present invention, there is provided a vector, comprising a first DNA sequence which is complementary to at least part of an alphavirus RNA genome and having the complement of complete alphavirus RNA genome replication regions; a second DNA sequence encoding a paramyxovirus protein or a protein fragment that generates antibodies that specifically react with the paramyxovirus protein; the second DNA sequence being inserted into a region of the first DNA sequence which is non-essential for replication; the first and second DNA sequences being under transcriptional control of a promoter.

The paramyxovirus protein may be selected from the group consisting of a parainfluenza virus (PIV) and a respiratory syncytial virus (RSV). The PIV protein may be PIV-1, PIV-2, PIV-3 or PIV-4, particularly the HN or F glycoproteins of PIV-3. The RSV protein particularly may be the F or G glycoprotein of RSV.

The second DNA sequence may encode a full length RSV F protein, or may encode a RSV F protein lacking the transmembrane anchor and cytoplasmic tail. The lack of the coding region for the transmembrane anchor and cytoplasmic tail results in a secreted form of the RSV F protein.

The second DNA sequence preferably encodes a RSV F protein and lacks a SpeI restriction site, and optionally, also lacking the transmembrane anchor and cytoplasmic tail encoding region. The absence of the SpeI restriction site may be carried out by mutating nucleotide 194 (T) of the RSV F gene to a C, which eliminates the SpeI without altering the amino acid sequence. The nucleotide sequence (SEQ ID No: 1) and encoded amino acid sequence (SEQ ID No: 2) of the mutated truncated RSV F gene is shown in FIG. 2.

The alphavirus preferably is a Semliki Forest virus and the first DNA sequence is the Semliki Forest viral sequence contained in plasmid pSFV1. The promoter used preferably is the SP6 promoter.

The vector may contain a unique restriction site permitting linearization of the vector without cleaving the second nucleotide sequence and maintaining the first and second nucleotides sequences under transcriptional control of the promoter. The unique restriction site preferably is a SpeI site, particularly that derived from pSFV1. The linearized form of the vector forms an embodiment herein.

The vector may be a plasmid vector, preferably one having the identifying characteristics of plasmid pMP37 (ATCC 97905) as shown in FIG. 1C and, more preferably, is the plasmid pMP37.

The mutant DNA sequence encoding an RSV F protein or a fragment thereof capable of inducing antibodies that specifically react with RSV F protein and lacking the SpeI restriction site present in the native DNA sequence, constitutes another aspect of the present invention. Such mutant DNA sequence lacking the SpeI site of the native sequence preferably is that shown in FIG. 2 (SEQ ID No: 1) or one which encodes the amino acid sequence shown in FIG. 2 (SEQ ID No: 2).

The novel vector provided herein may be linearized by cleavage at the unique restriction site and transcribed to an RNA transcript. In accordance with a further aspect of the invention, there is provided an RNA transcript of a vector as provided herein produced by linearization and transcription.

The RNA transcripts provided herein may be provided in the form of an immunogenic composition for in vivo administration to a host for the generation in the host of antibodies to paramyxovirus protein, such immunogenic compositions comprising, as the active component thereof, an RNA transcript as provided herein. Such immunogenic compositions, which are provided in accordance with another aspect of the invention, may be formulated with any suitable pharmaceutically-acceptable carrier for the in vivo administration and may produce a protective immune response.

In a yet further aspect of the present invention, there is provided a method of immunizing a host against disease caused by infection with paramyxovirus, which comprises administering to the host an effective amount of an RNA transcript as provided herein.

The present invention also includes a novel method of using a gene encoding a RSV F protein or an fragment of an RSV F protein capable of generating antibodies which specifically react with RSV F protein to protect a host against disease caused by infection with respiratory syncytial virus, which comprises isolating said gene; operatively linking said gene to a DNA sequence which is complementary to at least part of an alphavirus RNA genome and having the complement of complete alphavirus RNA genome replication regions in a region of said DNA sequence which is non-essential for replication to form a plasmid vector wherein said gene and DNA sequence are under transcriptional control of a promoter; linearizing the plasmid vector while maintaining said gene and DNA sequence under said transcriptional control of the promoter; forming an RNA transcript of said linearized vector; and introducing said RNA transcript to said host.

Linearizing the plasmid vector is effected by cleaving the plasmid vector at a unique restriction site therein at a location which permits the maintenance of the gene and the DNA sequence under the transcriptional control of the promoter. The unique restriction site may be an SpeI site, such as derived from plasmid pSFV1.

The plasmid vector employed preferably is plasmid pMP37 and the linearizing step is effected by cleavage at the SpeI site of plasmid pMP37 (see FIG. 1C).

In addition, the present invention includes a method of producing a vaccine for protection of a host against disease caused by infection with respiratory syncytial virus (RSV), which comprises isolating a first DNA sequence encoding an RSV F protein from which the transmembrane anchor and cytoplasmic tail are absent and lacking any SpeI restriction site; operatively linking said first DNA sequence to a second DNA sequence which is complementary to at least part of an alphavirus RNA genome and having the complete alphavirus genome replication regions in a region of said second DNA sequence which is non-essential for replication to form a plasmid vector wherein said first and second DNA sequences are under transcriptional control of a promoter; linearizing the plasmid vector while maintaining said first and second DNA sequences under said transcriptional control of the promoter; forming a RNA transcript of said linearized vector; and formulating said RNA transcript as a vaccine for in vivo administration.

Linearizing the plasmid vector is effected by cleaving the plasmid vector at a unique restriction site therein at a location which permits the maintenance of the gene and the DNA sequence under the transcriptional control of the promoter. The unique restriction site may be an SpeI site, such as derived from plasmid pSFV1.

The plasmid vector employed preferably is plasmid pMP37 and the linearizing step is effected by cleavage at the SpeI site of plasmid pMP37.

Advantages of the present invention include the c provision of RNA transcripts which are useful in generating an immune response by in vivo administration.

BRIEF DESCRIPTION OF THE FIGURES

The present invention will be further understood from the following description with reference to the drawings, in which:

FIGS. 1A, 1B and 1C show a scheme for construction of plasmid pMP37 used to generate the RSV-F RNA;

FIG. 2 shows the nucleotide sequence (SEQ ID No: 1) and deduced amino acid sequence (SEQ ID No: 2) of a truncated RSV F gene lacking the transmembrane anchor and cytoplasmic tail and mutated at nucleotide 194 to eliminate the SpeI restriction site present in the unmutated gene;

GENERAL DESCRIPTION OF INVENTION

Figure 1A:
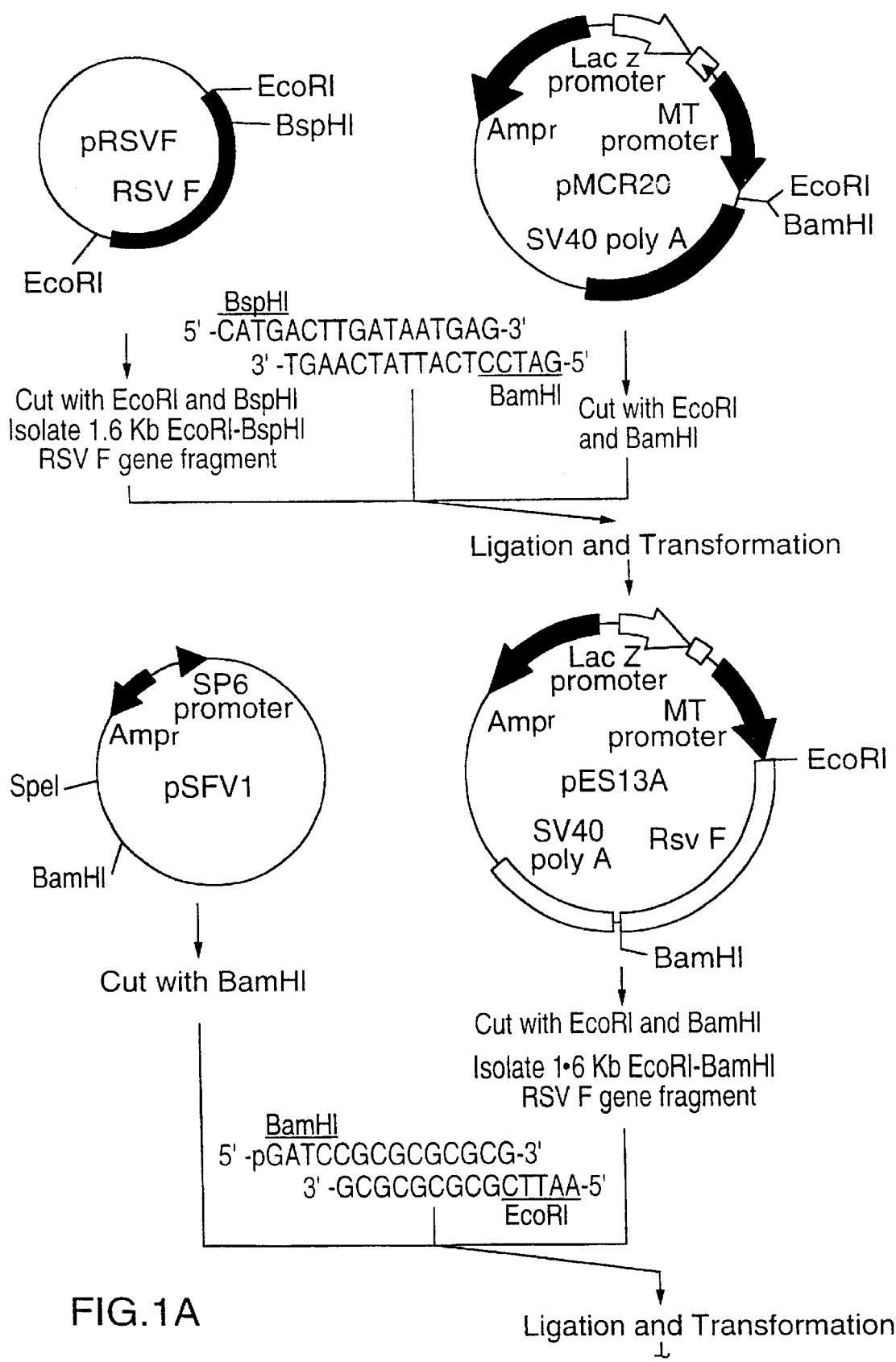

As described above, the present invention, in general, relates to protection of hosts against disease caused by infection by paramyxovirus by RNA immunization using RNA transcripts formed from DNA vectors by linearization and transcription of the linearized vector. In particular, the invention is concerned with protection of hosts against disease caused by infection by respiratory syncytial virus (RSV), although not specifically limited thereto. The description which follows refers specifically to employing DNA sequences and RNA transcripts thereof encoding RSV F protein and fragments thereof which generate antibodies which specifically react with RSV F protein.

In this application, the term "RSV F protein" is used to define a full-length RSV F protein, including proteins having variations in their amino acid sequences including those naturally occurring in various strain of RSV and those introduced by PCR amplification of the encoding gene while retaining the immunogenic properties, a secreted form of the RSV F protein lacking a transmembrane anchor and cytoplasmic tail, as well as fragments of RSV F protein capable of generating antibodies which specifically react with RSV F protein and functional analogs of RSV F protein. In this application, a first protein is a "functional analog" of a second protein if the first protein is immunologically related to and/or has the same function as the second protein. The functional analog may be, for example, a fragment of the protein or a substitution, addition or deletion mutant thereof.

A vector is constructed to contain a first DNA sequence which is complementary to at least part of an alphavirus RNA genome, specifically Semliki Forest virus, and having the complement of complete alphavirus RNA genome replication regions. A second DNA sequence encoding the RSV F protein is inserted into a region of the first DNA sequence which is non-essential for replication. The first and second DNA sequences are under transcriptional control of a promoter. The resulting vector is linearized and an RNA transcript formed from the linearized vector.

The RNA transcripts provided herein, when administered to an animal, including a human, replicate rapidly and effect in vivo RSV F protein expression, as demonstrated by an RSV F-protein specific antibody response in the animal to which it is administered. Such antibodies may be employed, if desired, in the detection of RSV protein in a sample.

As may be seen from the results detailed in the Examples below, the RNA transcripts provided a high anti-F IgG antibody titre with a IgG1/IgG2a ratio closely following the ratio obtained from immunization with live virus. Immunization with the RNA transcripts protected the animals against live RSV challenge.

It is clearly apparent to one skilled in the art, that the various embodiments of the present invention have many applications in the fields of vaccination, diagnosis and treatment of RSV infections. A further non-limiting discussion of such uses is further presented below.

1. Vaccine Preparation and Use

Immunogenic compositions, suitable to be used as vaccines, may be prepared from the RSV F gene and vectors as disclosed herein. The vaccine elicits an immune response in a subject which includes the production of anti-RSV F antibodies. Immunogenic compositions, including vaccines, containing the RNA transcripts may be prepared as injectables, in physiologically-acceptable liquid solutions or emulsions for polynucleotide administration. The RNA transcripts associated with liposomes, such as lecithin liposomes or other liposomes known in the art, as a nucleic acid liposome (for example, as described in WO 93/24640, ref. 38) or the RNA may be associated with an adjuvant, as described in more detail below. Liposomes comprising cationic lipids interact spontaneously and rapidly with polyanions, such as DNA and RNA, resulting in liposome/nucleic acid complexes that capture up to loot of the polynucleotide. In addition, the polycationic complexes fuse with cell membranes, resulting in an intracellular delivery of polynucleotide that bypasses the degradative enzymes of the lyposomal compartment. Published PCT application WO 94/27435 describes compositions for genetic immunization comprising cationic lipids and polynucleotides. Agents which assist in the cellular uptake of nucleic acid, such as calcium ions, viral proteins and other transfection facilitating agents, may advantageously be used.

Polynucleotide immunogenic preparations may also be formulated as microcapsules, including biodegradable time-release particles. Thus, U.S. Pat. No. 5,151,264 describes a particulate carrier of a phospholipid/glycolipid/polysaccharide nature that has been termed Bio Vecteurs Supra Moleculaires (BVSM). The particulate carriers are intended to transport a variety of molecules having biological activity in one of the layers thereof.

U.S. Pat. No. 5,075,109 describes encapsulation of the antigens trinitrophenylated keyhole limpet hemocyanin and staphylococcal enterotoxin B in 50:50 poly (DL-lactidecoglycolide). Other polymers for encapsulation are suggested, such as poly(glycolide), poly(DL-lactide-coglycolide), copolyoxalates, polycaprolactone, poly(lactide-co-caprolactone), poly(esteramides), polyorthoesters and poly(8-hydroxybutyric acid), and polyanhydrides.

Published PCT application WO 91/06282 describes a delivery vehicle comprising a plurality of bioadhesive microspheres and antigens. The microspheres being of starch, gelatin, dextran, collagen or albumin. This delivery vehicle is particularly intended for the uptake of vaccine across the nasal mucosa. The delivery vehicle may additionally contain an absorption enhancer.

The RNA transcripts may be mixed with pharmaceutically acceptable excipients which are compatible therewith. Such excipients may include water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously, intravenously, intradermally or intramuscularly, possibly following pretreatment of the injection site with a local anesthetic. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Oral formulations may include normally employed incipients, such as, for example, pharmaceutical grades of saccharine, cellulose and magnesium carbonate.

The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize the RSV F protein and antibodies thereto, and if needed, to produce a cell-mediated immune response. Precise amounts of active ingredient required to be administered depend on the judgment of the practitioner. However, suitable dosage ranges are readily determinable by one skilled in the art and may be of the order of about 1 µg to about 10 mg of the RSV F RNA. Suitable regimes for initial administration and booster doses are also variable, but may include an initial administration followed by subsequent administrations. The dosage may also depend on the route of administration and will vary according to the size of the host. A vaccine which protects against only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Immunogenicity can be significantly improved if the vectors are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Thus, adjuvants have been identified that enhance the immune response to antigens. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines.

A wide range of extrinsic adjuvants and other immunomodulating material can provoke potent immune responses to antigens. These include saponins complexed to membrane protein antigens to produce immune stimulating complexes (ISCOMS), plutonic polymers with mineral oil, killed mycobacteria in mineral oil, Freund's complete adjuvant, bacterial products, such as muramyl dipeptide (MDP) and lipopolysaccharide (LPS), as well as monophoryl lipid A, QS 21 and polyphosphazene.

In particular embodiments of the present invention, the RNA transcript comprising a first nucleotide sequence encoding an F protein of RSV may be delivered in conjunction with a targeting molecule to target the vector to selected cells including cells of the immune system.

The RNA transcript may be delivered to the host by a variety of procedures, for example, Tang et al. (ref. 39) disclosed that introduction of gold microprojectiles coated with DNA encoding bovine growth hormone (BGH) into the skin of mice resulted in production of anti-BGH antibodies in the mice, while Furth et al. (ref. 40) showed that a jet injector could be used to transfect skin, muscle, fat and mammary tissues of living animals.

Biological Deposits

Certain vectors that contain the gene encoding RSV F protein and referred to herein have been deposited with the American Type Culture Collection (ATCC) located at 10801 University Boulevard, Manassas, Va. 20110-2209, U.S.A., pursuant to the Budapest Treaty and prior to the filing of this application.

Samples of the deposited plasmids will become available to the public upon grant of a patent based upon this United States patent application and all restrictions on access to the deposits will be removed at that time. Non-viable deposits will be replaced in the event ATCC is unable to dispense the same. The invention described and claimed herein is not to be limited in scope by plasmids deposited, since the deposited embodiment is intended only as an illustration of the invention. Any equivalent or similar plasmids that encode similar or equivalent antigens as described in this application are within the scope of this invention.

Deposit Summary

| Plasmid | ATCC Designation | Date Deposited |
| --- | --- | --- |
| pMP37 | 97905 | Feb. 27, 1997 |

EXAMPLE

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry and immunology used but not explicitly described in this disclosure and these Examples are amply reported in the scientific literature and are well within the ability of those skilled in the art.

Example 1

This Example describes the construction of a Semliki Forest virus (SFV) expression vector containing a truncated version of the RSV F gene.

Figure 1B:
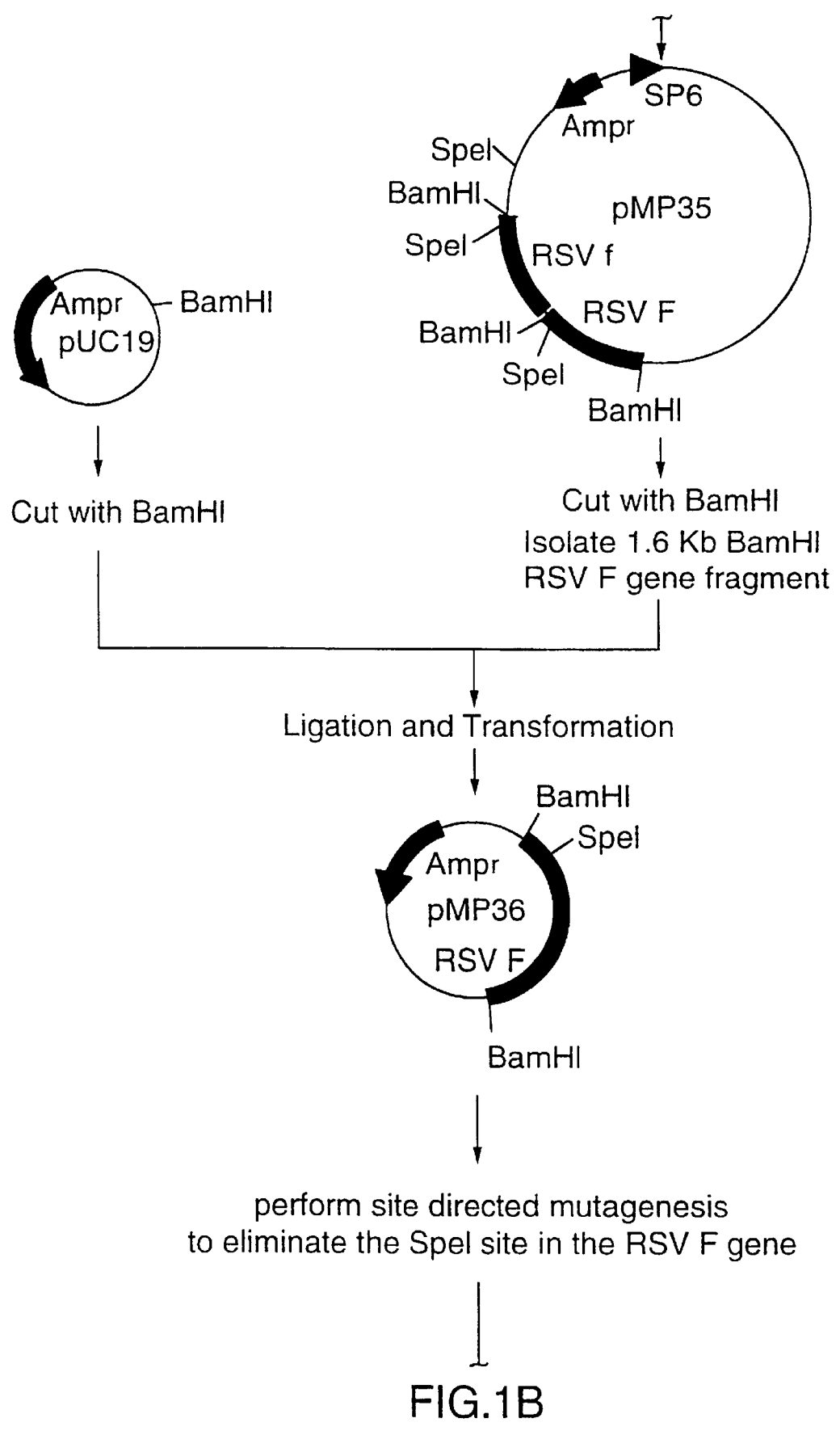
Figure 1C:
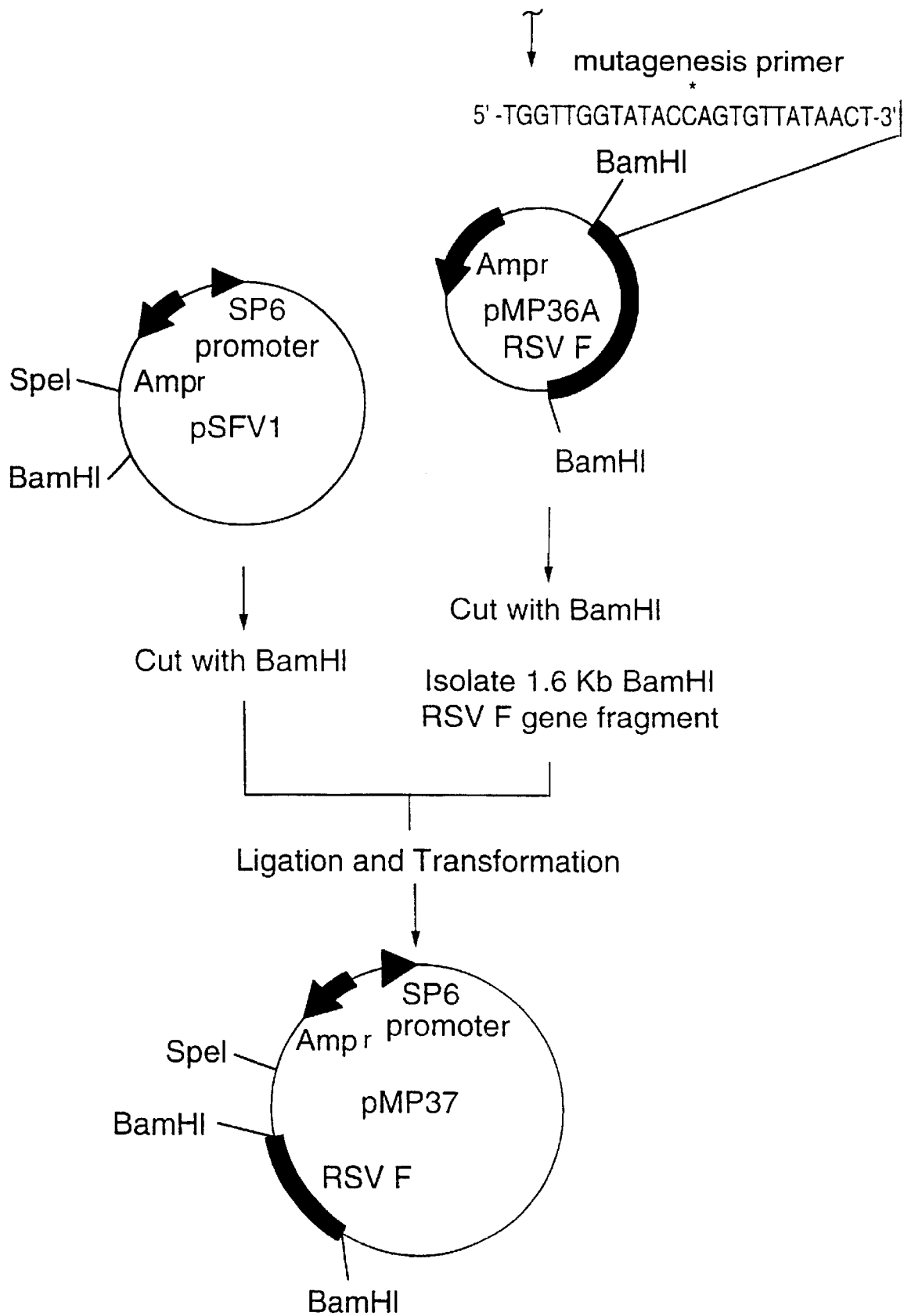

A truncated version of the RSV F gene was inserted into the SFV expression vector pSFV1 (Gibco BRL, Gaithersburg, Md., USA) according to the steps outlined in FIG. 1. The RSV F gene was originally cloned from a subtype A RSV clinical isolate into plasmid pRSV F, as fully described in copending U.S. patent application Ser. No. 08/001,554 filed Jan. 6, 1993, assigned to the assignee hereof and the disclosure of which is incorporated herein by reference, (ref. 41 and WO 93/14207). A fragment of the RSV F gene was excised from plasmid RSV F by digesting the plasmid with BspHI and EcoRI. The restriction enzyme BspHI cuts within the RSV F gene coding region, removing 48 amino acids from the C-terminus of the F protein. These amino acids make up most of the transmembrane domain and the entire cytoplasmic tail. The resulting 1.6 Kb truncated RSV F gene fragment was cloned into the EcoRI-BamHI sites of the Bluescript-based mammalian cell expression vector pMCR20 (Stratagene, La Jolla, Calif.) in a 3-way ligation with a linker, based upon the following sequence:

5' CATGACTTGATAATGAG 3' (SEQ ID No: 3)
3' TGAACTATTACTCCTAG 5' (SEQ ID No: 4)

to generate plasmid pES13A, as described in the aforementioned U.S. Ser. No. 08/001,554 (WO 93/14207). This linker adds a non-template encoded threonine to the truncated RSV F protein C-terminus and inserts three successive stop codons at the end of the truncated gene.

The 1.6 Kb truncated RSV F gene fragment was then excised from plasmid pES13A by digesting with EcoRI and BamHI. In another 3-way ligation, the 1.6 Kb EcoRI-BamHI RSV F gene fragment was cloned into the BamHI site of the SFV expression vector pSFV1 with another linker, based upon the following sequence:

5' GATCCGCGCGCGCG 3' (SEQ ID No: 5)
3' GCGCGCGCGCTTAA 5' (SEQ ID No: 6)

to generate plasmid pMP35. This plasmid contained two copies of the 1.6 Kb BamHI RSV F gene fragment. At this time, it was discovered that there was an SpeI site located in the RSV F gene fragment 193 bp from the upstream BamHI site. It is necessary to linearize a pSFV1 based plasmid with SpeI prior to its use in the in vitro transcription reaction described below. Therefore, the SpeI site in the RSV F gene needed to be removed and this was effected in the following manner.

The 1.6 Kb truncated RSV F gene fragment was excised from plasmid pMP35 by digesting with BamHI and ligated into the BamHI site of pUC19 to generate the plasmid pMP36. The Transformer™ site-directed mutagenesis kit (Clonetech, Palo Alto, Calif., USA) and a primer, 5'-TGGTTGGTATACCAGTGTTATAACT (SEQ ID No: 7) were used, according to the manufacturer's instructions, to change nucleotide 194 from a T to a C. This change eliminates the SpeI site in the RSV F gene without affecting the amino acid sequence of the encoded RSV F protein. The sequence of plasmid pMP36A, which contains the altered RSV F gene, was determined by DNA sequence analysis. The 1.6 Kb truncated RSV F gene fragment was excised from plasmid pMP36A by digesting with BamHI and ligated into the BamHI site of pSFV1 to generate plasmid pMP37 (ATCC 97905). Proper orientation of the truncated RSV F gene was confirmed by restriction mapping and DNA sequence analysis. FIG. 2 shows the nucleotide sequence (SEQ ID No: 1) of the truncated RSV F gene BamHI fragment with the SpeI site eliminated and the amino acid sequence (SEQ ID No: 2) of the secreted RSV F protein encoded thereby.

Plasmid DNA was purified using plasmid DNA mide kits from Qiagen (Chatsworth, Calif., USA), according to the manufacturer's instructions.

Example 2

This Example describes the preparation of SpeI linearized pMP37 required for the generation of SFV-RSVF RNA in in vitro transcription reactions and the preparation of SFV-RSVF RNA.

20 μg of plasmid pMP37, prepared as described in Example 1, was cut with SpeI in a 100 μL reaction containing 20 MM Tris-HCl (pH 7.4), 5 mM MgCl2, 50 mM KCl and 30 units of SpeI (Gibco BRL, Gaithersburg, Md., USA).

SFV-RNA was generated from the linearized plasmid in a 300 μL in vitro transcription reaction using of the following materials 40 mM Tris-HCl (pH 7.9)
6 mM $MgCl_2$
2 mM spermidine-$(HCl)_3$
1 mM DTT (dithiothreonol)
1 mM ATP (adenosine triphosphate)
1 mM GTP (guanosine triphosphate)
1 mM CTP (cytidine triphosphate)
1 mM UTP (uridine triphosphate)
1 mM $m^7G(5')ppp(5')G$ RNA cap analog (New England Biolabs, Mississauga, Ont., Canada)
360 units of RNasin® enzyme inhibitor (Promega, Madison, Wis., USA)
270 units of SP6 RNA polymerase (Gibco BRL, Gaithersburg, Md., USA)

The reaction was incubated at 37° C. for 50 minutes. The SFV-RSVF RNA so produced was purified from the salt, enzymes, unincorporated NTP's and cap analog by passing the reaction mix through CHROMA SPIN™-200 DEPC-$H_2O$ columns (Clonetech, Palo Alto, Calif., USA) (75 μL/column) according to the manufacturer's instructions. The purified RNA then was ethanol precipitated and resuspended in DEPC-treated $H_2O$ to a final concentration of 1 μg/μL. The purified RNA was mixed with an equal volume of 2×PBS just prior to immunization.

Example 3

This Example describes the immunization of mice with SFV-RSVF RNA and the immunogenicity results obtained.

It has previously been shown that mice are susceptible to infection with RSV (ref. 42) and are a relevant animal model. The mice were immunized with the SFV-RSVF RNA prepared as described in Example 2, by the intramuscular (i.m.) route. The anterior tibialis muscles of five BALB/c mice (female 6 to 8 week old) (Jackson Lab., Bar Harbour, Me., USA) were bilaterally injected with 2×25 μg (0.5 μg/μL) of the PBS-directed SFV-RSVF RNA. Five days prior to RNA immunization, the muscles were treated with 2×50 μL of cardiotoxin (10 μM in PBS) (Latoxan, France). Treatment of muscles with cardiotoxin has previously been shown to enhance the uptake of DNA and enhance the immune response (ref. 43). These mice were boosted in an identical manner 4 weeks later (Table 1 below). The control groups were immunized with (1) SFV RNA expressing β-galactosidase (SFV-LacZ RNA), (2) SFV-RSVF RNA as prepared herein; (3) live RSV, (4) PBS with alum and RSV subunit preparation with alum. These mice were also boosted in an identical manner 4 weeks later (Table 1). The RSV subunit preparation, comprising RSV F, G and M proteins is described in copending U.S. patent application Ser. No. 08/679,060 filed Jul. 12, 1996 now U.S. Pat. No. 6,020,182, assigned to the assignee hereof and the disclosure of which is incorporated herein by reference (WO 98/02457).

Two weeks after the second immunization, mice were challenged intranasally with $10^6$ plaque forming units (pfu) of the A2 strain of RSV (BG-4A). Animals were sacrificed 4 days later. Lungs were aseptically removed, weighed, and homogenized in 2 mL of complete culture medium. The virus titre in lung homogenates was determined in duplicate using Vero cells, as previously described (ref. 44).

Sera was obtained from the mice at 4 and 6 weeks. Anti-RSV F antibody titres (IgG, IgG1 and IgG2a) in these sera were determined by enzyme-linked immunosorbent assay (ELISA), as described in Example 4. The RSV-specific plaque reduction titres of these sera were determined as previously described (ref. 44).

Figure 3A:
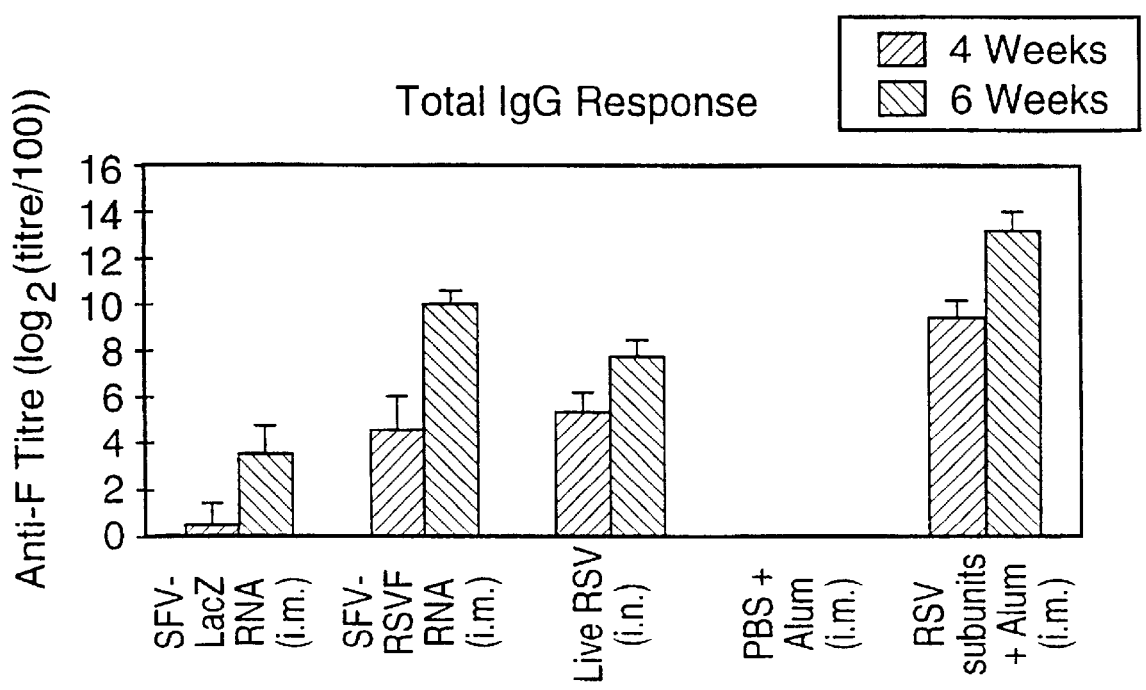
FIG. 3, comprising panels A, B and C, shows the anti-RSV F titres in sera from mice taken 4 weeks after primary immunization and 2 weeks after boosting with the RSV F RNA. Panels A, B, and C show total IgG response, IgG1 response and IgG2a response respectively.
Figure 3B:
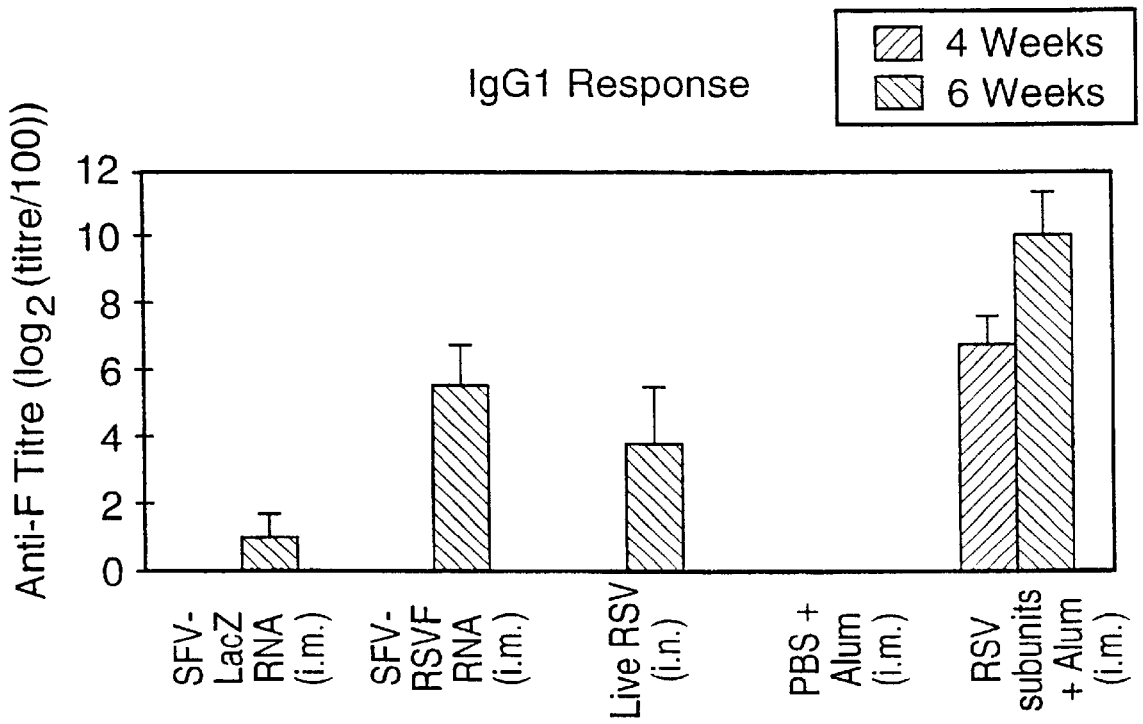
Figure 3C:
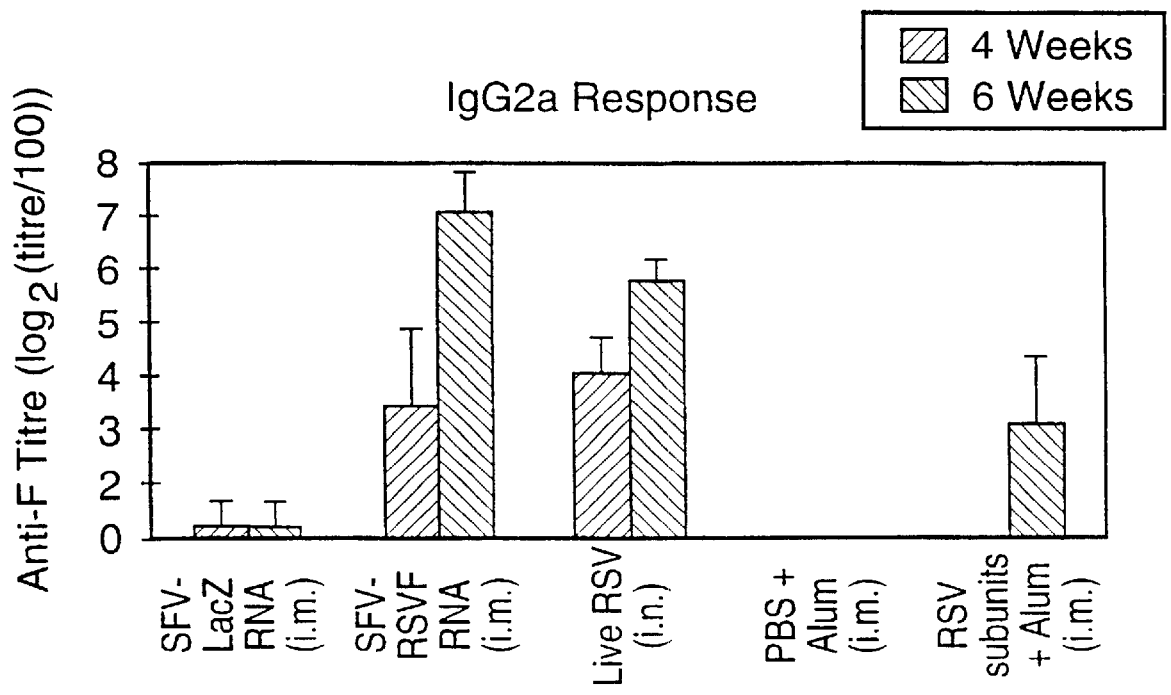

The anti-RSV F antibody responses in the sera of BALB/c mice that were immunized as outlined in Table 1 are summarized in FIG. 3. The animals immunized with SFV-RSVF RNA, live RSV, or RSV subunit preparation+alum all had high total anti-RSV F IgG antibody titres in their serum at both 4 and 6 weeks (FIG. 3, panel A). However, the IgG1/IgG2a ratios differed markedly, as seen from FIG. 3, panels B and C. The sera from animals that were immunized with live RSV had an anti-F IgG1/IgG2a ratio of approximately 0.69 after 6 weeks. This value is in contrast to the anti-RSV F IgG1/IgG2a ratio obtained in mice after 6 weeks that were primed and boosted with the alum-adjuvanted RSV subunit preparation. In this case, the anti-RSV IgG1/IgG2a ratio was approximately 4.3. The anti-RSV F IgG1/IgG2a ratios obtained in mice immunized with SFV-RSVF RNA after 6 weeks were 0.79. These results suggest that immunization of mice with the SFV-RSVF RNA results in more of a Th-1 type response similar to that obtained with live RS virus rather than the Th-2 type response seen with the alum-adjuvanted RSV subunit preparation.

Figure 4:
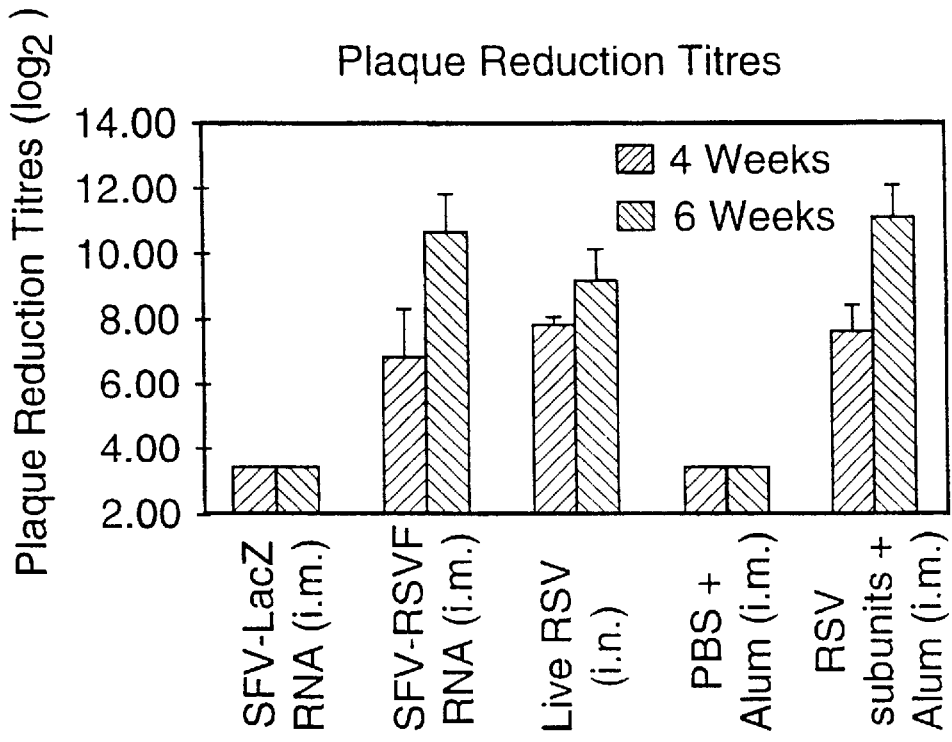
FIG. 4 shows the RSV-specific neutralizing antibody titres expressed as plaque reduction titres for various RSV preparations.

As shown in FIG. 4, the sera of mice that were primed and boosted with the various RSV preparations as outlined in Table 1, all had significant levels of RSV-specific neutralizing antibodies (groups 2, 3 and 5). In contrast to the placebo control animals (groups 1 and 4), the lower respiratory tract of mice that were immunized with SFV-RSVF RNA, live RSV, or the alum-adjuvanted RSV subunit preparation, were completely protected against live RS virus challenge, as seen in Table 2.

Immunization of mice with the SFV-RSVF RNA protected mice against live RSV challenge. The protective ability of this SFV replicon was comparable to that induced by inoculation with live RSV or alum—adjuvanted RSV subunits. The type of immune response generated appeared to be more of a Th-1 like response similar to that elicited by live RSV.

Example 4

This Example describes the determination of anti-RSV F antibody titres.

Nunc-MaxiSorp plate wells were coated overnight at room temperature with 2.5 ng of immunoaffinity-purified RSV F protein diluted in 0.05M carbonate-bicarbonate buffer, pH 9.6. Wells were blocked for non-specific binding by adding 0.1% BSA in PBS for 30 min. at room temperature, followed by two washes in a washing buffer of 0.1% BSA in PBS+0.1% Tween 20. Serial two or four-fold dilutions of mouse serum was added to the wells. After a one hour incubation at room temperature, plates were washed five times with washing buffer, and horseradish peroxidase (HRP) labeled conjugate was added at the appropriate optimal dilution in washing buffer. The total IgG assay used $F(ab')_2$ goat antimouse IgG (H+L specific)-HRP from Jackson Immuno Research Laboratory Inc. (Baltimore Md., USA). Sheep anti-mouse IgG1 -HRP from Serotec (Toronto, Ontario, Canada) was used in the IgG1 assay and goat anti-mouse IgG2a from Caltag Laboratories (San Francisco, Calif., USA) was used in the IgG2a assay. Following one hour incubation at room temperature, the plates were washed five times with washing buffer, and hydrogen peroxide (substrate) in the presence of tetramethylbenzidine was added. The reaction was stopped by adding 2 M sulfuric acid. The colour was read in a Multiscan Titertek plate reader at an optical density (OD) of 450 nm. The titre was taken as the reciprocal of the last dilution at which the OD was approximately double. This OD must be greater that the negative control of the assay at the starting dilution. The pre-immune serum of each animal was used as the negative control.

SUMMARY OF THE DISCLOSURE

In summary of this disclosure, there are provided novel vectors containing DNA sequences encoding a paramyxovirus protein, particularly a RSV F protein, which can be linearized and transcribed to RNA for in vivo administration to generate a protective immune response to disease caused by infection by paramyxovirus, particularly respiratory syncytial virus. Modifications are possible within the scope of this invention.

TABLE 1

Immunization protocol

| GROUP | PRIME | ROUTE OF INOCULATION | BOOST | ROUTE OF INOCULATION |
|---|---|---|---|---|
| 1 | SFV-LacZ RNA[1] | Intramuscular | SFV-LacZ RNA[1] | Intramuscular |
| 2 | SFV-RSVF RNA[1] | Intramuscular | SFV-RSVF RNA[1] | Intramuscular |
| 3 | Live RSV[2] | Intranasal | Live RSV[2] | Intranasal |
| 4 | PBS + alum | Intramuscular | PBS + alum | Intramuscular |
| 5 | RSV subunits + alum[3] | Intramuscular | RSV subunits + alum[3] | Intramuscular |

Mice were inoculated with:
[1] 25 µg of RNA was injected into each hind leg muscle in 50 µL of PBS
[2] 2.5 × 10⁵ pfu of mouse-adapted A2 virus
[3] 1 µg of RSV subunit vaccine adsorbed to alum (1.5 mg/dose)

TABLE 2

| | Antigen Formulation | | Mean Virus Lung Titre ($\log_{10}$/g ± s.d.) | ? protection |
|---|---|---|---|---|
| GROUP | Prime | Boost | | |
| 1 | SFV-LacZ RNA | SFV-LaCZ RNA | 4.18 ± 0.06 | 0 |
| 2 | SFV-RSVF RNA | SFV-RSVF RNA | ≦1.83 ± 0 | 100 |
| 3 | Live RSV | Live RSV | ≦1.83 ± 0 | 100 |
| 4 | PBS + alum | PBS + alum | 4.17 ± 0.17 | 0 |
| 5 | RSV subunits + alum | RSV subunits + alum | ≦1.83 ± 0 | 100 |

Reference

1. McIntosh K. and Chanock R. M. in Fields B. N. and Knipe D. M. (eds). Virology. Raven Press, New York, 1990, pp.1045–1072.
2. Murphy B. R., Hall S. L., Kulkarni A. B., Crowe J. E., Collins P. L., Connors M., Karron R. A. and Chanock R. M., Virus Res 32, 13–36, 1994.
3. Osterweil D. and Norman D., Am Geriat Soc 36, 659–662, 1990.

4. Agius G., Dindinand G., Biggar R. J., Peyre R., Vaillant V., Ranger S., Poupet J. Y., Cisse M. F. and Casters M., J Med Virol 30, 117–127, 1990.
5. Katz S. L. in New vaccine development establishing priorities Vol 1. National Academic Press, Washington, 1985, pp. 3974 09.
6. Wertz G. W. and Sullender W. M., Biotechnology 20, 151–176, 1992.
7. Fulginiti V. A., Eller J. J., Sieber O. F., Joyner J. W., Minamitani M. and Meiklejohn G., Am i Epidemiol 89, 449–463, 1969.
8. B. Chin J., Magoffin R. L., Shearer I. A., Schieble J. H. and Lennette E. H., Am J Epidemiol 89, 449–463, 1969.
9. Belshe R. B., Van Voris L. P. and Mufson M. A., J Infect Dis 145, 311–319, 1982.
10. Kim R. M., Arrobio J. O., Pyles G., Brandt C. D., Camargo E., Chanock R. M. and Parrott R. H., Pediatrics 48, 745–755, 1971.
11. Gruber C. and Levine S., J Gen Virol 64, 825–832, 1983.
12. Olmstead R. A., Elango N. and Prince G. A., Proc Natl Acad Sci USA 83, 7462–7466, 1991.
13. Parrington M., Cockle S., Wyde P., Du R. -P., Snell E., Yan W.-Y., Wang Q., Gisonni L., Sanhueza S., Ewasyshyn M. and Klein M., Virus Genes 14, 65–74, 1997
14. Fulginiti, V. A., Eller, J. J., Sieber, O. F., Joyner, J. W., Minamitani, M. and Meiklejohn, G. (1969) Am. J. Epidemiol. 89 (4), 435–448.
15. Chin, J., Magoffin, R. L., Shearer, L. A., Schieble, J. H. and Lennette, E. H. (1969) Am. J. Epidemiol. 89 (4), 449–463.
16. Jensen, K. E., Peeler, B. E. and Dulworth, W. G. (1962) J. Immunol. 89, 216–226.
17. Murphy, B. R., Prince, G. A., Collins, P. L., Van Wyke -Coelingh, K., Olmsted, R. A., Spriggs, M. K., Parrott, R. H., Kim, H.-Y., Brandt, C. D. and Chanock, R. M. (1988) Vir. Res. 11, 1–15.
18. Hall, S. L., Sarris, C. M., Tierney, E. L., London, W. T., and Murphy, B. R. (1993) J. Infect. Dis. 167, 958–962.
19. Belshe, R. B., Karron, R. A., Newman, F. K., Anderson, E. L., Nugent, S. L., Steinhoff, M., Clements, M. L., Wilson, M. H., Hall, S. L., Tierney, E. L. and Murphy, B. R. (1992) J. Clin. Microbiol. 30 (8), 2064–2070.
20. Hall, S. L., Stokes, A., Tierney, E. L., London, W. T., Belshe, R. B., Newman, F. C. and Murphy, B. R. (1992) Vir. Res. 22, 173–184.
21. Van Wyke Coelingh, K. L., Winter, C. C., Tierney, E. L., London, W. T. and Murphy, B. R. (1988) J. Infect. Dis. 157 (4), 655–662.
22. Ray, R., Novak, M., Duncan, J. D., Matsuoka, Y. and Compans, R. W. (1993) J. Infect. Dis. 167, 752–755.
23. Ray, R., Brown, V. E. and Compans, R. W. (1985) J. Infect. Dis. 152 (6), 1219–1230.
24. Ray, R. and Compans, R. W. (1987) J. Gen. Virol. 68, 409–418.
25. Ray, R., Glaze, B. J., Moldoveanu, Z. and Compans, R. W. (1988) J. Infect. Dis. 157 (4), 648–654.
26. Ray, R., Matsuoka, Y., Burnett, T. L., Glaze, B. J. and Compans, R. W. (1990) J. Infect. Dis. 162, 746–749.
27. Ray, R., Glaze, B. J. and Compans, R. W. (1988) J. Virol. 62 (3), 783–787.
28. Ewasyshyn, M., Caplan, B., Bonneau A.-M., Scollard, N., Graham, S., Usman, S. and Klein, M. (1992) Vaccine 10 (6), 412–420.
29. Ambrose, M. W., Wyde, P. R., Ewasyshyn, M., Bonneau, A.-M., Caplan, B., Meyer, H. L. and Klein, M. (1991) Vaccine 9, 505–511.
30. Kasel, J. A., Frank, A. L., Keitel, W. H., Taber, L. H., Glezen W. P. J. Virol. 1984; 52:828–32.
31. Lehman, D. J., Roof, L. L., Brideau, R. J., Aeed, P. A., Thomsen, D. R., Elhammer, A. P., Wathen, M. W. and Homa, F. L. (1993) J. Gen. Virol. 74, 459–469.
32. Brideau, R. J., Oien, N. L., Lehman, D. J., Homa, F. L. and Wathen, M. W. (1993) J. Gen. Virol. 74, 471–477.
33. Ebata, S. N., Prevec, L., Graham, F. L. and Dimock, K. (1992) Vir. Res. 24, 21–33.
34. Hall, S. L., Murphy, B. R. and Van Wyke Coelingh, K. L. (1991) Vaccine 9, 659–667.
35. Strauss E. G. and Strauss J. H., in Schlesinger S. S. and Schlesinger M. i. (eds). The Togaviridae and Flaviviridae. Plenum Press, New York, 1986, pp. 35–90.
36. Liljestrom P. and Garoff H., Biotechnology 9, 1356–1361, 1991.
37. Zhou X., Berglund P., Rhodes G., Parker S. E., Jondal M. and Liljestrom P., Vaccine 12, 1510–1514, 1994.
38. Dalemans W., Delers A., Delmelle C., Denamur F., Meykens R., Thiriart C., Veenstra S., Francotte M., Bruck C. and Cohen J., Annals New York Academy of Sciences, 255–256, 1996.
39. Tang et al, Nature 1992, 356: 152–154.
40. Futh et al, Analytical Biochemistry, 1992, 205: 365–368.
41. Du, R. P. et al., Biotechnology 12, 813–818, 1994
42. Graham B. S., Perkins M. D., Wright P. F. and Karzon D. T., J. Mod. Virol. 26, 153–162, 1988.
43. Davis et al. Vaccine 12, 1503–1509, 1994.
44. Prince, G. A., et al. Am. J. Pathol. 93, 771–790, 1978.

I claim:

1. A vector, comprising:
    a first DNA sequence which is complementary to at least part of an alphavirus RNA genome and having a complement of complete alphavirus RNA genome replication regions, and
    a second DNA sequence which encodes an RSV F protein and lacks a SpeI restriction site and lacks a transmembrane anchor and cytoplasmic tail encoding region, said second DNA sequence having a nucleotide sequence selected from the group consisting of SEQ ID No: 1 and a nucleotide sequence encoding SEQ ID No: 2,
    said second DNA sequence being inserted into a region of said first DNA sequence which is non-essential for replication thereof,
    said first and second DNA sequences being under transcriptional control of a promoter.

2. The vector of claim 1 wherein said alphavirus is a Semliki Forest virus.

3. The vector of claim 2 wherein said first DNA sequence is the Semliki Forest virus sequence contained in plasmid pSFV1.

4. The vector of claim 2 wherein said promoter is the SP6 promoter.

5. The vector of claim 1 which is a plasmid vector having a unique restriction site permitting linearization of the vector without cleaving the second DNA sequence.

6. The vector of claim 5 wherein the unique restriction site is SpeI site.

7. The vector of claim 7 wherein the SpeI site is derived from plasmid pSFV1.

8. The vector of claim 1 is in a linearized form.

9. An RNA transcript of the vector of claim 1.

10. The RNA transcript of claim 9 which is derived by linearization of a plasmid vector of claim 1 at a unique restriction site provided in the vector and permitting linearization of the vector without cleaving the second DNA sequence and transcribing the linearized vector.

11. The RNA transcript of claim 9 wherein, in said vector, said alphavirus is a Semliki Forest virus.

12. The RNA transcript of claim 11 wherein, in said vector, said first DNA sequence is the Semliki Forest virus sequence contained in plasmid pSFV1.

13. The RNA transcript of claim 11 wherein, in said vector, said promoter is the SP6 promoter.

14. An immunogenic composition for in vivo administration to a host for the generation in the host of antibodies to paramyxoviridae protein, comprising, as the active component thereof, an RNA transcript as claimed in claim 9.

15. The immunogenic composition of claim 14 for the generation of protective antibodies in the host.

16. A method of immunizing a host against disease caused by infection with paramyxovirus, which comprises administering to said host an effective amount of an RNA transcript as claimed in claim 9.

17. A mutant DNA sequence encoding an RSV F from which is absent an SpeI restriction site present in the non-mutant sequence, said mutant DNA sequence lacking a transmembrane anchor and cytoplasmic tail encoding region.

18. The mutant DNA sequence of claim 17 wherein nucleotide 194 (T) of a non-mutant RSV F gene is mutated to a C to eliminate the SpeI site in the non-mutant RSV F gene.

19. A mutant DNA molecule sequence lacking an SpeI site present in the non-mutant sequence and encoding a truncated RSV F protein and having the DNA sequence shown in FIG. 2 (SEQ ID No:1) or having a DNA sequence encoding the amino acid sequence shown in FIG. 2 (SEQ ID No: 2).

20. A method of using a gene encoding a respiratory syncytial virus (RSV) F protein to protect a host against infection caused by RSV, which comprises:

isolating said gene, said gene lacking a SpeI restriction site and encoding a RSV F protein that lacks a transmembrane anchor and cytoplasmic tail, said gene having a nucleotide sequence selected from the group consisting of SEQ ID No: 1 and a nucleotide sequence encoding SEQ ID No: 2, operatively linking said gene to a DNA sequence which is complementary to at least part of an alphavirus RNA gemone and having the complement of complete alphavirus RNA genome replication regions in a region of said DNA sequence which is non-essential for replication to form a plasmid vector wherein said gene and DNA sequence are under transcriptional control of a promoter, linearizing the plasmid vector while maintaining said gene and DNA sequence under said transcriptional control of the promoter, forming an RNA transcript of said linearized vector, and introducing said RNA transcript to a host.

21. The method of claim 20 wherein said linearizing of the plasmid vector is effected by cleaving the plasmid vector at a unique restriction site therein at a location which permits the maintenance of the gene and DNA sequence under transcriptional control of the promoter.

22. The method of claim 21 wherein the unique restriction site is an SpeI site.

* * * * *

SEQUENCE LISTING

```
<160> NUMBER OF SEQ ID NOS: 7

<210> SEQ ID NO 1
<211> LENGTH: 1623
<212> TYPE: DNA
<213> ORGANISM: respiratory syncytial virus

<400> SEQUENCE: 1
gatccgcgcg cgcgaattcg gcacgagtaa caatggagtt gctaatcctc aaagcaaatg      60
caattaccac aatcctcact gcagtcacat tttgttttgc ttctggtcaa aacatcactg     120
aagaatttta tcaatcaaca tgcagtgcag ttagcaaagg ctatcttagt gctctgagaa     180
```

-continued

```
ctggttggta taccagtgtt ataactatag aattaagtaa tatcaaggaa aataagtgta    240
atggaacaga tgctaaggta aaattgataa acaagaatt  agataaatat aaaaatgctg    300
taacagaatt gcagttgctc atgcaaagca caccaccaac aaacaatcga gccagaagag    360
aactaccaag gtttatgaat tatacactca acaatgccaa aaaaaccaat gtaacattaa    420
gcaagaaaag gaaaagaaga tttcttggtt ttttgttagg tgttggatct gcaatcgcca    480
gtggcgttgc tgtatctaag gtcctgcacc tagaagggga agtgaacaag atcaaaagtg    540
ctctactatc cacaaacaag gctgtagtca gcttatcaaa tggagttagt gtcttaacca    600
gcaaagtgtt agacctcaaa aactatatag ataaacaatt gttacctatt gtgaacaagc    660
aaagctgcag catatcaaat atagaaactg tgatagagtt ccaacaaaag aacaacagac    720
tactagagat taccagggaa tttagtgtta atgcaggtgt aactacacct gtaagcactt    780
acatgttaac taatagtgaa ttattgtcat taatcaatga tatgcctata acaaatgatc    840
agaaaaagtt aatgtccaac aatgttcaaa tagttagaca gcaaagttac tctatcatgt    900
ccataataaa agaggaagtc ttagcatatg tagtacaatt accactatat ggtgttatag    960
atacaccctg ttgaaaacta cacacatccc ctctatgtac aaccaacaca aagaagggt   1020
ccaacatctg tttaacaaga actgacagag gatggtactg tgacaatgca ggatcagtat   1080
ctttcttccc acaagctgaa acatgtaaag ttcaatcaaa tcgagtattt tgtgacacaa   1140
tgaacagttt aacattacca agtgaaataa atctctgcaa tgttgacata ttcaacccca   1200
aatatgattg taaaattatg acttcaaaaa cagatgtaag cagctccgtt atcacatctc   1260
taggagccat tgtgtcatgc tatggcaaaa ctaaatgtac agcatccaat aaaaatcgtg   1320
gaatcataaa gacattttct aacgggtgcg attatgtatc aaataaaggg atggacactg   1380
tgtctgtagg taacacatta tattatgtaa ataagcaaga aggtaaaagt ctctatgtaa   1440
aaggtgaacc aataataaat ttctatgacc cattagtatt cccctctgat gaatttgatg   1500
catcaatatc tcaagtcaac gagaagatta ccagagcct  agcatttatt cgtaaatccg   1560
atgaattatt acataatgta aatgctggta atccaccac  aaatatcatg acttgataat   1620
gag                                                                 1623
```

<210> SEQ ID NO 2
<211> LENGTH: 527
<212> TYPE: PRT
<213> ORGANISM: respiratory syncytial virus

<400> SEQUENCE: 2

```
Met Glu Leu Leu Ile Leu Lys Ala Asn Ala Ile Thr Thr Ile Leu Thr
  1               5                  10                  15

Ala Val Thr Phe Cys Phe Ala Ser Gly Gln Asn Ile Thr Glu Glu Phe
                 20                  25                  30

Tyr Gln Ser Thr Cys Ser Ala Val Ser Lys Gly Tyr Leu Ser Ala Leu
             35                  40                  45

Arg Thr Gly Trp Tyr Thr Ser Val Ile Thr Ile Glu Leu Ser Asn Ile
         50                  55                  60

Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Pro Thr Asn Asn Arg Ala Arg Arg Glu Leu Pro
            100                 105                 110
```

-continued

```
Arg Phe Met Asn Tyr Thr Leu Asn Asn Ala Lys Lys Thr Asn Val Thr
        115                 120                 125
Leu Ser Lys Lys Arg Lys Arg Arg Phe Leu Gly Phe Leu Leu Gly Val
    130                 135                 140
Gly Ser Ala Ile Ala Ser Gly Val Ala Val Ser Lys Val Leu His Leu
145                 150                 155                 160
Glu Gly Glu Val Asn Lys Ile Lys Ser Ala Leu Leu Ser Thr Asn Lys
                    165                 170                 175
Ala Val Val Ser Leu Ser Asn Gly Val Ser Val Leu Thr Ser Lys Val
                180                 185                 190
Leu Asp Leu Lys Asn Tyr Ile Asp Lys Gln Leu Leu Pro Ile Val Asn
        195                 200                 205
Lys Gln Ser Cys Ser Ile Ser Asn Ile Glu Thr Val Ile Glu Phe Gln
    210                 215                 220
Gln Lys Asn Asn Arg Leu Leu Glu Ile Thr Arg Glu Phe Ser Val Asn
225                 230                 235                 240
Ala Gly Val Thr Thr Pro Val Ser Thr Tyr Met Leu Thr Asn Ser Glu
                245                 250                 255
Leu Leu Ser Leu Ile Asn Asp Met Pro Ile Thr Asn Asp Gln Lys Lys
                260                 265                 270
Leu Met Ser Asn Asn Val Gln Ile Val Arg Gln Gln Ser Tyr Ser Ile
        275                 280                 285
Met Ser Ile Ile Lys Glu Glu Val Leu Ala Tyr Val Val Gln Leu Pro
    290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
                340                 345                 350
Pro Gln Ala Glu Thr Cys Lys Val Gln Ser Asn Arg Val Phe Cys Asp
        355                 360                 365
Thr Met Asn Ser Leu Thr Leu Pro Ser Glu Ile Asn Leu Cys Asn Val
    370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
                420                 425                 430
Lys Thr Phe Ser Asn Gly Cys Asp Tyr Val Ser Asn Lys Gly Met Asp
        435                 440                 445
Thr Val Ser Val Gly Asn Thr Leu Tyr Tyr Val Asn Lys Gln Glu Gly
    450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Lys Ser Asp Glu Leu
                500                 505                 510
Leu His Asn Val Asn Ala Gly Lys Ser Thr Thr Asn Ile Met Thr
        515                 520                 525
```

-continued

```
<210> SEQ ID NO 3
<211> LENGTH: 17
<212> TYPE: DNA
<213> ORGANISM: respiratory syncytial virus

<400> SEQUENCE: 3
catgacttga taatgag                                                  17

<210> SEQ ID NO 4
<211> LENGTH: 17
<212> TYPE: DNA
<213> ORGANISM: respiratory syncytial virus

<400> SEQUENCE: 4
tgaactatta ctcctag                                                  17

<210> SEQ ID NO 5
<211> LENGTH: 14
<212> TYPE: DNA
<213> ORGANISM: respiratory syncytial virus

<400> SEQUENCE: 5
gatccgcgcg cgcg                                                     14

<210> SEQ ID NO 6
<211> LENGTH: 14
<212> TYPE: DNA
<213> ORGANISM: respiratory syncytial virus

<400> SEQUENCE: 6
gcgcgcgcgc ttaa                                                     14

<210> SEQ ID NO 7
<211> LENGTH: 25
<212> TYPE: DNA
<213> ORGANISM: respiratory syncytial virus

<400> SEQUENCE: 7
tggttggtat accagtgtta taact                                         25
1
2
```